United States Patent
Dowlatshahi (10) Patent No.: US 7,041,109 B2
(45) Date of Patent: May 9, 2006

(54) APPARATUS AND METHOD FOR INTERSTITIAL LASER THERAPY OF SMALL BREAST CANCERS AND ADJUNCTIVE THERAPY

(75) Inventor: Kambiz Dowlatshahi, Chicago, IL (US)

(73) Assignee: Kelsey, Inc., Chicago, IL (US)

( * ) Notice: Subject to any disclaimer, the term of this patent is extended or adjusted under 35 U.S.C. 154(b) by 122 days.

(21) Appl. No.: 10/319,765

(22) Filed: Dec. 12, 2002

(65) Prior Publication Data

US 2004/0116914 A1    Jun. 17, 2004

(51) Int. Cl.
*A61B 19/10*    (2006.01)

(52) U.S. Cl. .................. 606/130; 606/10; 606/170; 378/37; 378/177; 378/195; 5/601

(58) Field of Classification Search .......... 606/10–18, 606/127–130, 167, 170; 600/564–567; 604/19–22; 5/601; 378/37, 177–180, 195–197, 206
See application file for complete search history.

(56) References Cited

U.S. PATENT DOCUMENTS

| | | | |
|---|---|---|---|
| 5,078,142 A | | 1/1992 | Siczek et al. |
| 5,169,396 A | | 12/1992 | Dowlatshahi et al. |
| 5,222,953 A | | 6/1993 | Dowlatshahi |
| 5,240,011 A | * | 8/1993 | Assa .................. 600/564 |
| 5,386,447 A | * | 1/1995 | Siczek .................. 378/37 |
| 5,415,169 A | * | 5/1995 | Siczek et al. .............. 600/427 |
| 5,569,240 A | | 10/1996 | Dowlatshahi et al. |
| 5,615,430 A | * | 4/1997 | Nambu et al. ............... 5/600 |
| 5,735,264 A | * | 4/1998 | Siczek et al. .............. 600/408 |
| 5,853,366 A | | 12/1998 | Dowlatshahi |
| 5,983,424 A | * | 11/1999 | Naslund .................. 5/601 |
| 6,058,322 A | * | 5/2000 | Nishikawa et al. .......... 600/408 |
| 6,094,760 A | * | 8/2000 | Nonaka et al. ................. 5/601 |
| 6,341,893 B1 | * | 1/2002 | Matsumoto et al. ......... 378/209 |
| 6,456,684 B1 | * | 9/2002 | Mun et al. .................. 378/20 |
| 6,569,176 B1 | * | 5/2003 | Jesseph .................. 606/167 |
| 6,928,672 B1 | * | 8/2005 | Pastyr et al. ............. 5/81.1 HS |

OTHER PUBLICATIONS

Dowlatshahi et al. "Stereotactically Guided Laser Therapy of Occult Breast Tumors," Arch Surg. vol. 135, 1345-1352, Nov. 2000.*
HAUSTED's brochure titled "Mammography/Biopsy Chair," 1993.*
Mammomat 3000 Nova Brochure written by Siemens, published prior to 2000.
Multifunctional Mammography—High Patient Throughput, Favorable Economics Brochure written by Siemens, published in 1999.
Mammography Biopsy Chair Brochure written by Hausted, published in 1993.
Sonoline Antaers—A New Dimension in Ultrasound Brochure written by Siemens, published prior to 2002.

* cited by examiner

*Primary Examiner*—A. Farah
(74) *Attorney, Agent, or Firm*—Bell, Boyd & Lloyd LLC (57) ABSTRACT

Apparatus and method for performing interstitial laser therapy and adjunctive therapy on a patient are revealed. The apparatus employs a combination of a mammography unit, an interstitial laser treatment device attached to the mammography unit and a treatment platform positioned relative to the mammography unit to enable the interstitial laser therapy to be performed. The use of the treatment platform with the mammography unit enables the interstitial laser therapy to be performed and, if necessary, adjunctive therapy to be performed in the same treatment room without transferring the patient to a new platform.

20 Claims, 8 Drawing Sheets

APPARATUS AND METHOD FOR INTERSTITIAL LASER THERAPY OF SMALL BREAST CANCERS AND ADJUNCTIVE THERAPY

BACKGROUND OF THE INVENTION

1. Field of the Invention

The present application relates to an apparatus and method for conducting interstitial laser therapy on tumors, such as breast tumors, and adjunctive therapy on the same treatment table and in the same treatment room. The apparatus employs a combination of a mammography unit, an interstitial laser treatment device which operates with the mammography unit, and a mammography/biopsy chair positioned relative to the mammography unit to enable the interstitial laser therapy and axillary lymph node surgery (sentinel node biopsy) to be performed.

2. Description of the Related Art

Percutaneous in situ or on-site treatment of malignant breast tumors is being developed in part due to the fact that breast cancer is being detected at earlier stages because of the increasing number of women receiving mammograms annually. If breast cancer and other cancers or tumors are detected in an early stage of development, they can be effectively treated by minimal surgery or by using an ablative agent such as laser energy, applied to the tumor for its destruction within the breast.

Mammography is the roentgenography or X-ray of the mammary gland. A mammography unit allows a physician to screen a breast for a tumor. A rotatable/positionable mammography unit with stereotactic capability allows a physician to do even more, i.e., screen a breast for a tumor, locate the tumor and obtain a biopsy of the tumor. Addition of digital technology to mammography assists the physician to process the image better and faster. In other words, a digital mammography unit functions as a screening unit, a diagnostic work-up system and a stereotactic biopsy unit.

The widespread practice of screening mammography and the increasing awareness of women as to its benefits has resulted in a growing number of tumors smaller than one cm being detected. Diagnosis of these non-palpable breast tumors is made by stereotactic or ultrasound-guided core biopsy, a less invasive procedure than wire localization and excisional biopsy. Currently, the favored local treatment of such tumors is by lumpectomy plus either axillary node dissection or sentinel node biopsy followed by chemo-radiation therapy.

Image-guided laser treatments of malignant tumors such as, breast, liver, head and neck tumors, have been in development for more than a decade. For example, U.S. Pat. No. 5,169,396 (Dowlatshahi et al.) is directed to the interstitial application of laser radiation therapy to tumor masses. In general, the apparatus includes a laser probe having a thin metallic cannula for insertion into a tumor mass, a laser for generating light having a chosen wavelength and intensity and an optical fiber for receiving and transmitting the laser light to the tumor mass. In operation, the optical fiber is inserted into the cannula such that a chosen physiologically acceptable fluid can flow coaxially between the cannula and the optical fiber. In addition, a heat sensing member or temperature probe is inserted adjacent into the tumor mass for monitoring the tumor temperature. The devitalized tumor is gradually cleared by the body immune system and within six months is replaced with a scar.

The current known technique for performing interstitial laser therapy for breast tumor includes having the patient lie face down on a platform of a stereotactic table. The patient's breast having the tumor extends through an aperture defined by the platform. The table supports a mechanism positioned below the platform for performing the interstitial laser therapy with the laser probe and in one embodiment a temperature probe.

One problem with such stereotactic tables is that some patients' breast are too small to extend fully to the necessary position adjacent to the mechanism for performing the interstitial laser therapy with the laser probe and temperature probe.

Other problems with stereotactic tables used for performing interstitial laser therapy for breast tumor are (1) the operator (surgeon) must work below or under the table in a cramped space and (2) axillary lymph node surgery cannot be done in that position. In other words, the patient has to be moved from the stereotactic table and transferred to a more appropriate treatment table, usually located in another treatment room, for any adjuvant operation.

In operations and many other procedures, including adjunctive therapies, where blood loss is possible, a patient must be placed on a suitable operating table or the like which has an inverted head position. One such adjunctive therapy procedure related to interstitial laser therapy for treating breast tumors includes the removal of one or more of the patient's lymph nodes. In the event that the patient's blood pressure drops during the procedure, a doctor can place the patient in an inverted head position to direct more blood to the patient's head to avoid any period of time where an insufficient amount of blood is being provided to the patient's brain. An insufficient amount of blood to a patient's brain can, of course, result in brain damage or death.

Additionally, stereotactic tables are relatively expensive. Accordingly, there is a need for a relatively inexpensive apparatus and method for conducting interstitial laser therapy and adjunctive therapies in the same treatment room without requiring the patient to move to a different platform or a different treatment room.

SUMMARY OF THE INVENTION

The present invention overcomes the above-recited problems by providing an apparatus and method for conducting interstitial laser therapy and adjunctive therapy on the same table (platform) and in the same treatment room.

The method for performing interstitial laser therapy and adjunctive therapy on a patient comprises the steps of a) placing the patient on an apparatus, the apparatus comprising a mammography unit, an interstitial laser treatment device attached to the mammography unit, where the device comprises a laser probe and a treatment platform positioned relative to the mammography unit to enable the interstitial laser therapy to be performed, where the apparatus is located in a single treatment room, where the treatment platform comprises a first platform surface, and where adjunctive therapy may be performed in the treatment room without transferring the patient to a second platform surface; b) performing a mammographic examination on the patient; c) analyzing results from the mammographic examination to determine whether interstitial laser therapy alone or interstitial laser therapy with adjunctive therapy should be performed on the patient; and d) performing interstitial laser therapy alone or interstitial laser therapy with adjunctive therapy on the patient.

In preferred embodiments of the method, the mammography unit is a rotatable/positionable digital mammography unit; the interstitial laser treatment mechanism further comprises a temperature probe; the treatment platform has at least two positions including a patient lying position and an inverted head position; and/or the adjunctive therapy comprises axillary node dissection or sentinel node biopsy.

In another preferred embodiment of the method, the treatment platform has at least three positions including a patient sitting position, a patient lying position and an inverted head position.

In yet other preferred embodiments of the method, the treatment platform is supported on wheels; the wheels comprise a stationary mechanism; and/or the stationary mechanism is selected from the group consisting of a locking mechanism, a positioning mechanism and combinations thereof.

In a more preferred embodiment of the method, the mammography unit is a rotatable/positionable digital mammography unit; the interstitial laser treatment device further comprises a temperature probe; the treatment platform has at least three positions including a patient sitting position, a patient lying position and an inverted head position; and the adjunctive therapy comprises axillary node dissection or sentinel node biopsy.

The apparatus for performing interstitial laser therapy and adjunctive therapy on a patient comprises
  a) a mammography unit;
  b) an interstitial laser treatment device attached to the mammography unit, where the mechanism comprises a laser probe; and
  c) a treatment platform positioned relative to the mammography unit to enable the interstitial laser therapy to be performed,
where the apparatus is located in a single treatment room, where the treatment platform comprises a first platform surface, and where adjunctive therapy may be performed in the treatment room without transferring the patient to a second platform surface.

In preferred embodiments of the apparatus, the mammography unit is a rotatable/positionable digital mammography unit; the interstitial laser treatment device further comprises a temperature probe; the treatment platform has at least three positions including a patient sitting position, a patient lying position and an inverted head position; and/or the adjunctive therapy comprises axillary node dissection or sentinel node biopsy.

In another preferred embodiment of the apparatus, the treatment platform has at least three positions including a patient sitting position, a patient lying position and an inverted head position.

In yet other preferred embodiments of the apparatus, the treatment platform is supported on wheels; the wheels comprise a stationary mechanism; and/or the stationary mechanism is selected from the group consisting of a locking mechanism, a positioning mechanism and combinations thereof.

In a more preferred embodiment of the apparatus, the mammography unit is a rotatable/positionable digital mammography unit; the interstitial laser treatment device further comprises a temperature probe; the treatment platform has at least three positions including a patient sitting position, a patient lying position and an inverted head position; and the adjunctive therapy comprises axillary node dissection or sentinel node biopsy.

DETAILED DESCRIPTION

Figure 1:
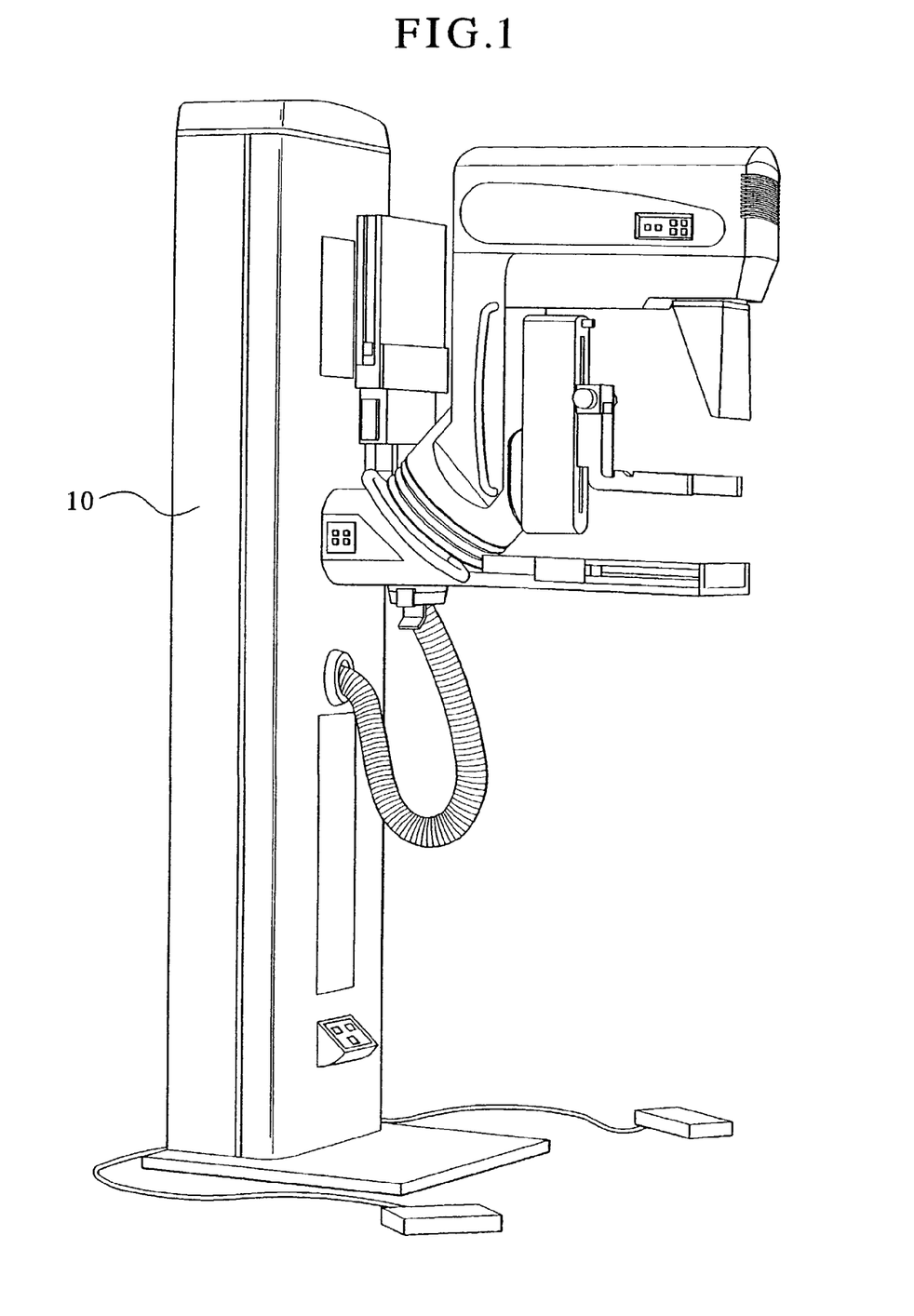
FIG. 1 is a schematic representation of a rotatable/positionable digital mammography unit with a biopsy device.
Figure 4:
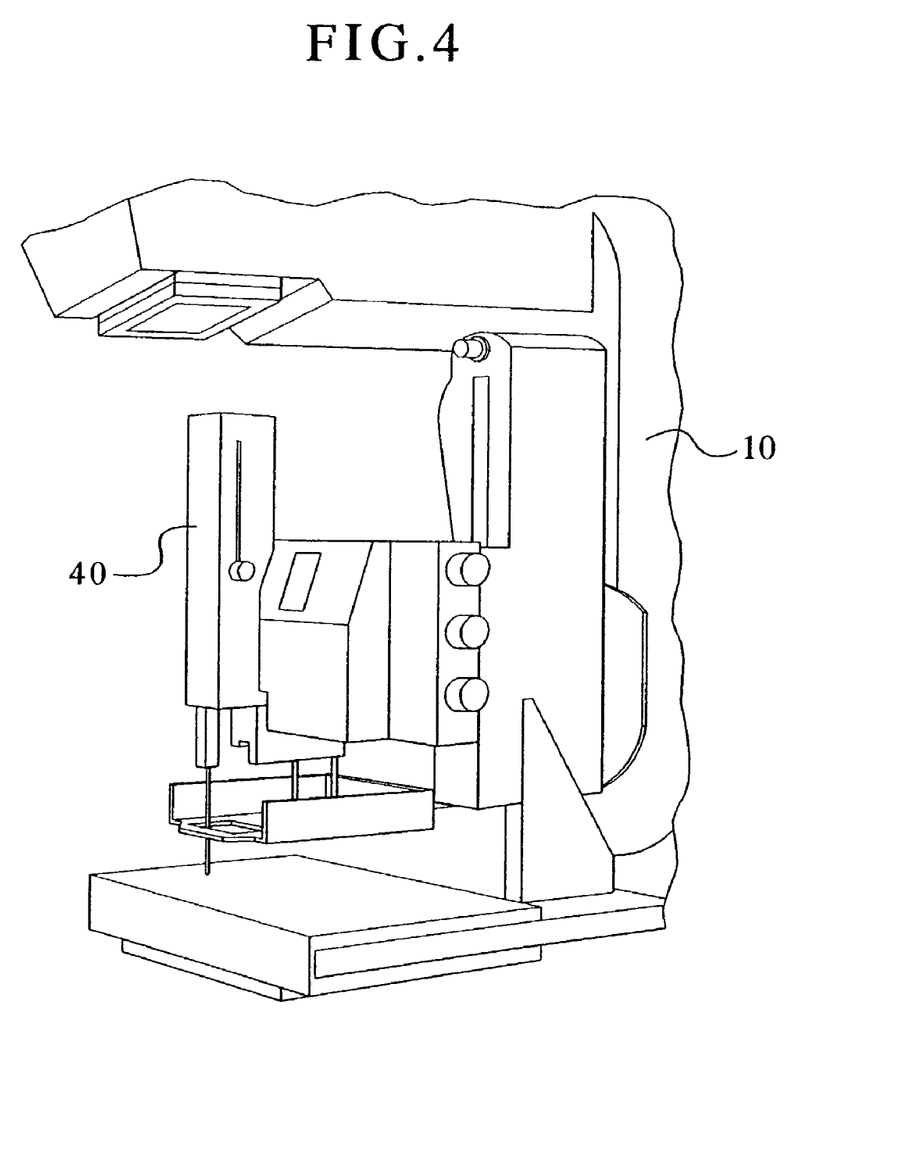
FIG. 4 is a schematic representation of a close up of the biopsy device mounted on a cut away view of the mammography unit in the present invention.
Figure 5:
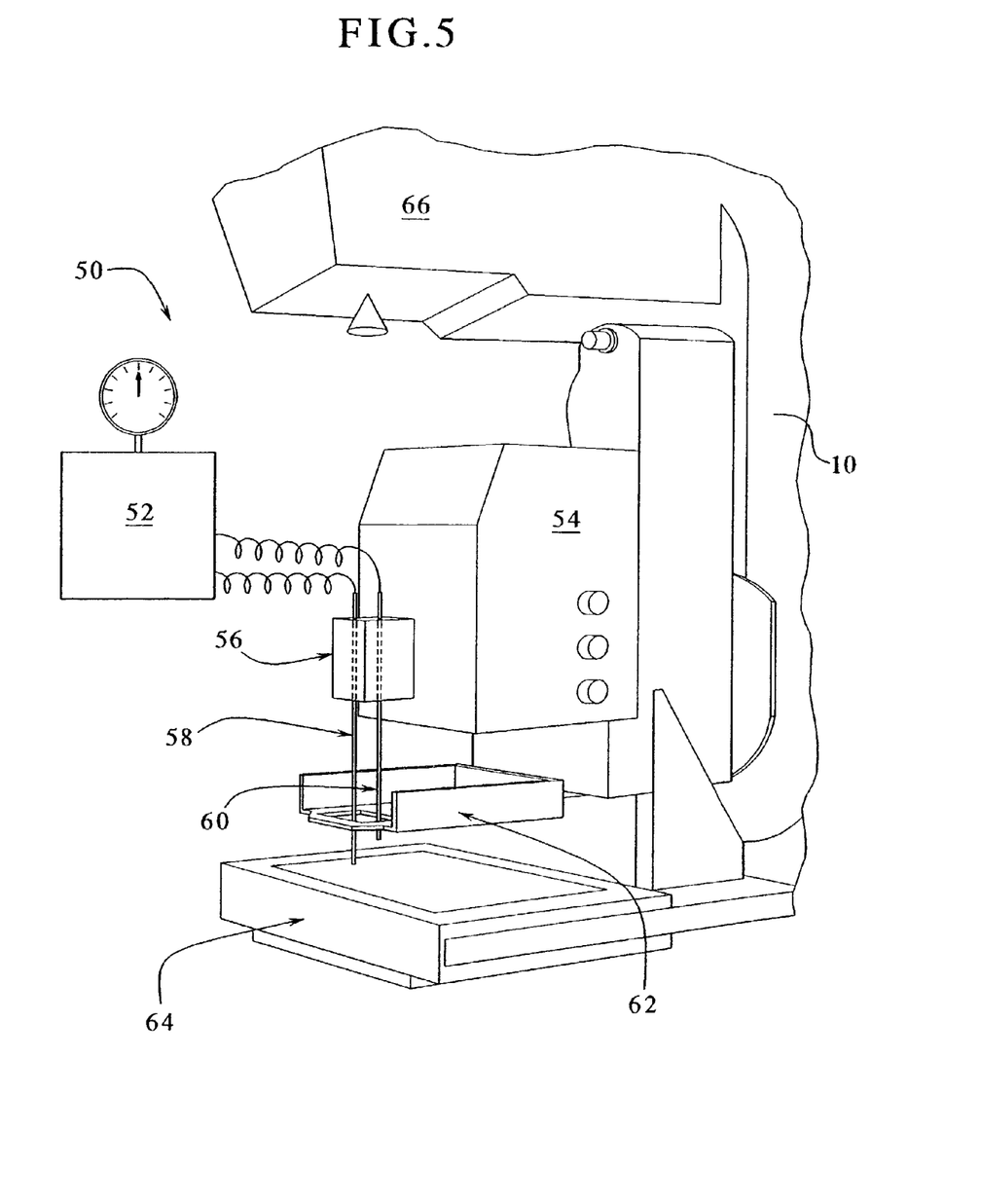
FIG. 5 is a schematic representation of a close up of the interstitial laser treatment device mounted on a cut away view of the mammography unit in the present invention.

The present invention employs a combination of a mammography unit, an interstitial laser treatment mechanism attached to the mammography unit and a treatment platform positioned relative to the mammography unit to enable the interstitial laser therapy to be performed. FIG. 1 is a schematic representation of a rotatable/positionable digital mammography unit 10 with a mounted biopsy device. FIG. 4 is a schematic representation of a close up of the biopsy device 40 mounted on the mammography unit in the present invention. FIG. 5 is a schematic representation of a close up of the interstitial laser treatment device 50 mounted on the mammography unit in the present invention. The biopsy device 40 and the interstitial laser treatment device 50 can be mounted separately on the mammography unit 10 in the present invention.

Figure 2A:
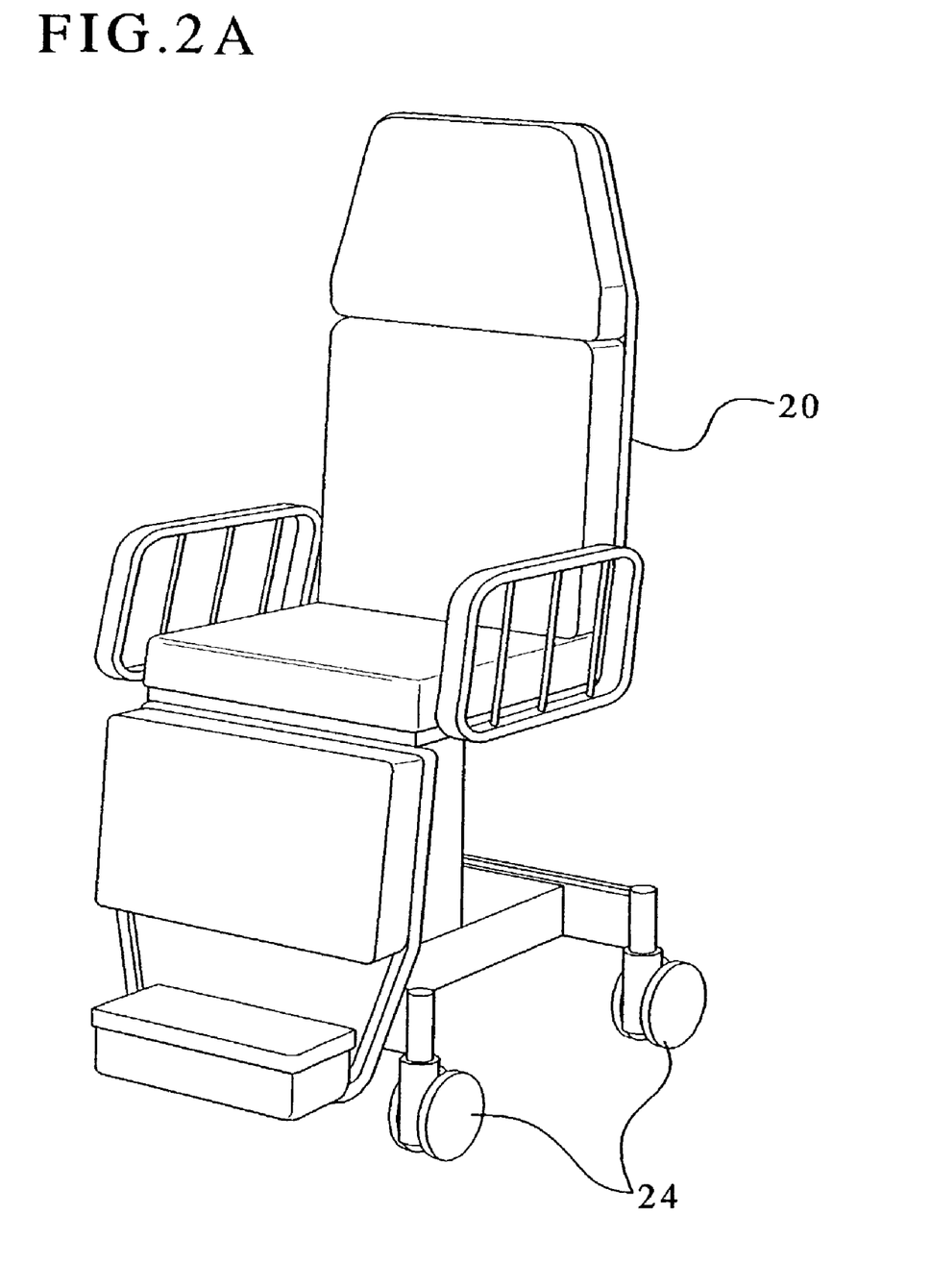
FIG. 2A is a schematic representation of a treatment platform in a patient sitting or seated position.
Figure 2B:
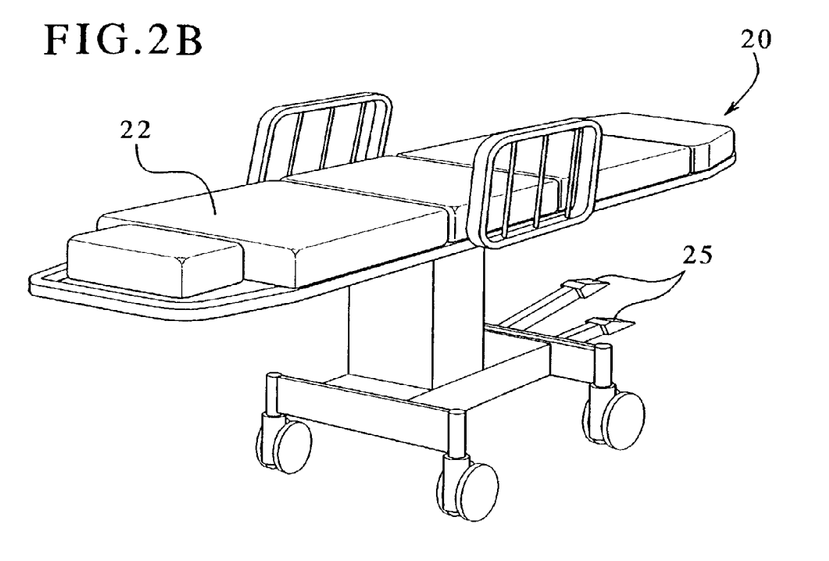
FIG. 2B is a schematic representation of the treatment platform in a patient lying or bed position.
Figure 2C:
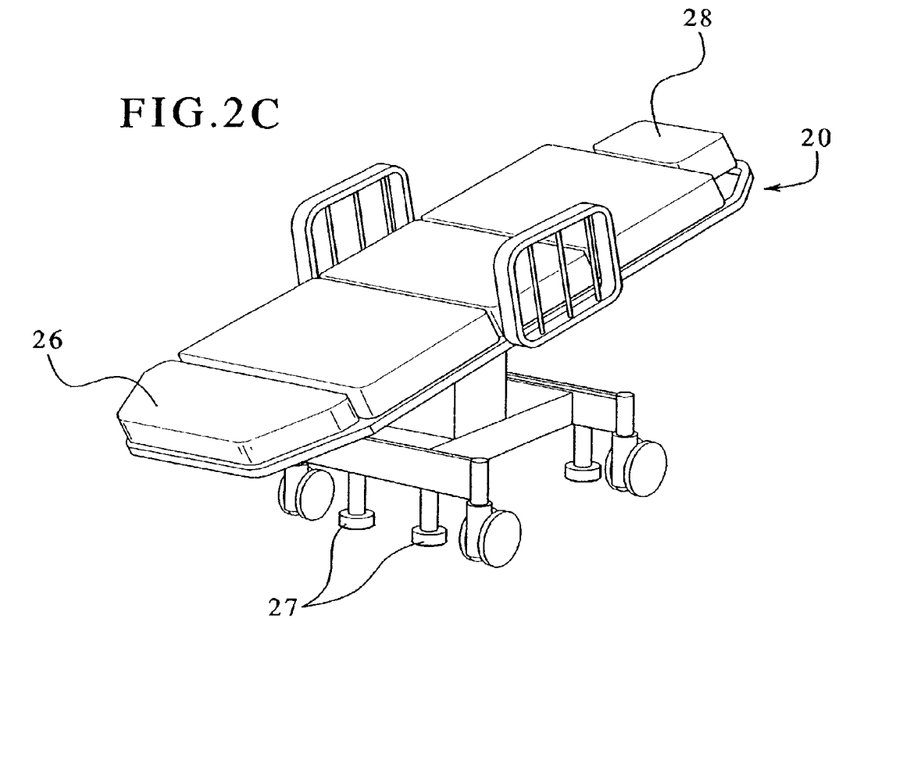
FIG. 2C is a schematic representation of the treatment platform in an inverted head or slanted bed position.

The treatment platform 20 has at least two positions including a patient lying position, FIG. 2B, and an inverted head position, FIG. 2C. In a preferred embodiment, the treatment platform 20 has a third position, i.e., a patient sitting position, FIG. 2A.

In addition, the treatment platform 20 is supported on wheels 24. One or more of the wheels 24 contains a stationary mechanism which when engaged prevents the treatment platform 20 from moving. The stationary mechanism can comprise a locking mechanism on the wheels or a positioning mechanism to lift the wheels from the floor. In FIG. 2A–2C, the treatment platform is shown as a mammography/biopsy chair. FIG. 2B shows an example of one type of locking mechanism 25 and FIG. 2C shows an example of one type of positioning mechanism 27.

The use of the treatment platform with the mammography unit enables the interstitial laser therapy to be performed and, if necessary, adjunctive therapy to be performed in the same treatment room without transferring the patient to a new platform.

FIG. 2A is a schematic representation of the treatment platform 20 in a patient sitting or seated position. FIG. 2B is a schematic representation of the treatment platform 20 in a patient lying or bed position and indicating the platform 22 surface.

In operations and many other procedures, including adjunctive therapies, where blood loss is possible, a patient must be placed on a suitable operating table or the like which has an inverted head position. One such adjunctive therapy procedure related to interstitial laser therapy for treating breast tumors includes the removal of one or more of the patient's lymph nodes. In the event that the patient's blood pressure drops during the procedure, a doctor can place the patient in an inverted head position to direct more blood to the patient's head to avoid any period of time where an insufficient amount of blood is being provided to the patient's brain. An insufficient amount of blood to a patient's brain can, of course, result in brain damage or death.

FIG. 4 is a schematic representation of a close up of the biopsy device 40 mounted on the mammography unit in the present invention. FIG. 5 is a schematic representation of a close up of the interstitial laser treatment device 50 mounted on the mammography unit in the present invention. Thus, both the biopsy device 40 and the interstitial laser treatment device 50 are mounted on the mammography unit 10 in the present invention.

FIG. 4 is a schematic representation of a close up of the biopsy device 40 mounted on the mammography unit in the present invention. FIG. 5 is a schematic representation of a close up of the interstitial laser treatment device 50 mounted on the mammography unit in the present invention. FIG. 5 shows a laser device 52, a stereotactic device 54, a needle holder 56, a laser needle or probe 58, a thermal needle or probe 60, a compression plate 62, a digital image receptor 64 and the X-ray tube 66 from the mammography unit 10.

Both the biopsy device 40 and the interstitial laser treatment device 50 are mounted on the mammography unit 10 in the present invention. At the time of treatment, the biopsy device 40 can be detached from the mammography unit 10 and replaced with the interstitial laser treatment device 50.

With the present invention, the treatment platform is easily and quickly converted from either a patient sitting position or a patient lying position to an inverted head or slanted bed position. FIG. 2C is a schematic representation of the treatment platform 20 in an inverted head or slanted bed position. The head end 26 and the foot end 28 of the treatment platform 20 in the inverted head or slanted bed position are indicated in FIG. 2C.

Figure 3A:
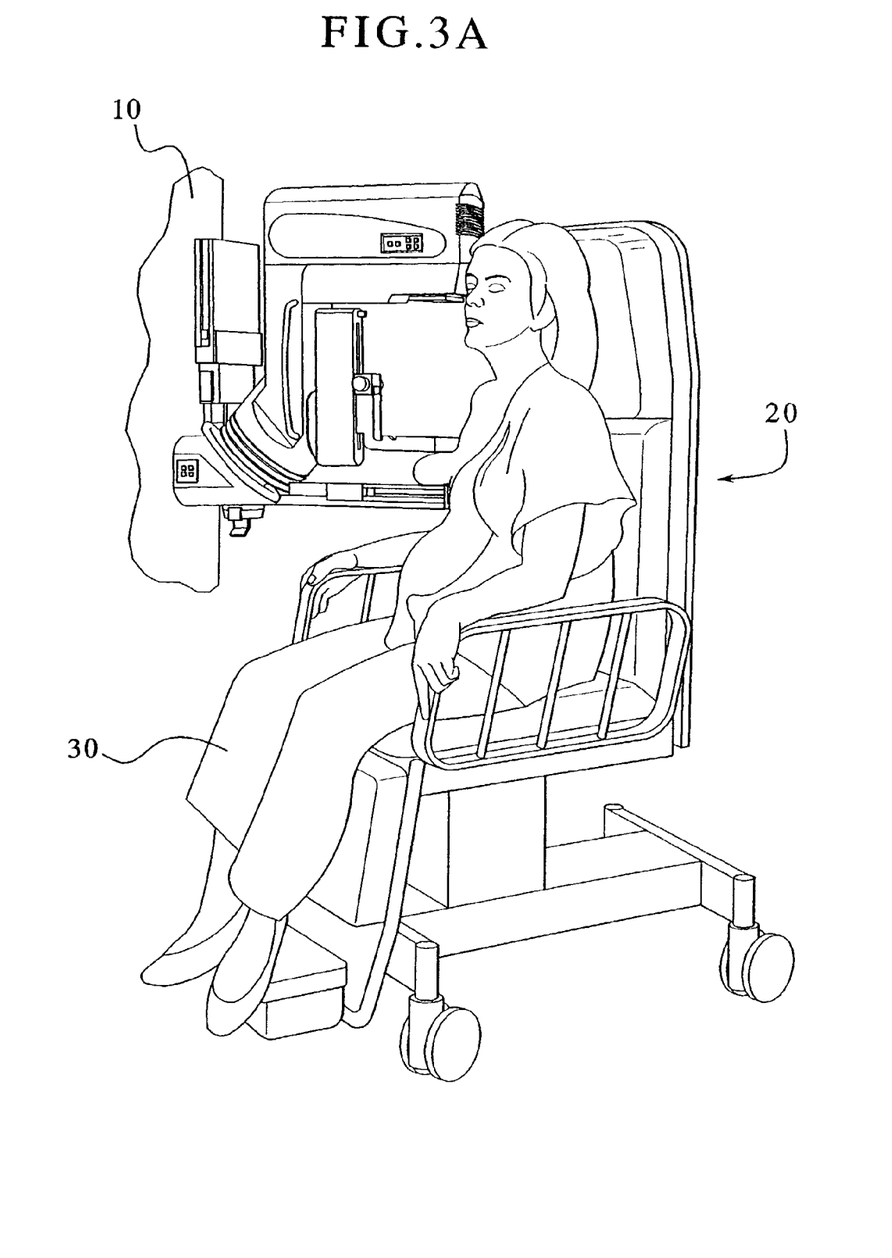
FIG. 3A is a schematic representation of a patient on the treatment platform in a sitting or seated position relative to a cut away view of the rotatable/positionable digital mammography unit.

FIG. 3A is a schematic representation of a patient 30 on a treatment platform 20 in a sitting or seated position relative to a cut away view of the rotatable/positionable digital mammography unit 10.

As mentioned above, with the present invention, a patient does not have to be removed from the platform of the treatment table and transferred to a more appropriate treatment table for any related or adjunctive therapies or procedures. In addition, all therapies and procedures are performed in a single treatment room.

Figure 3B:
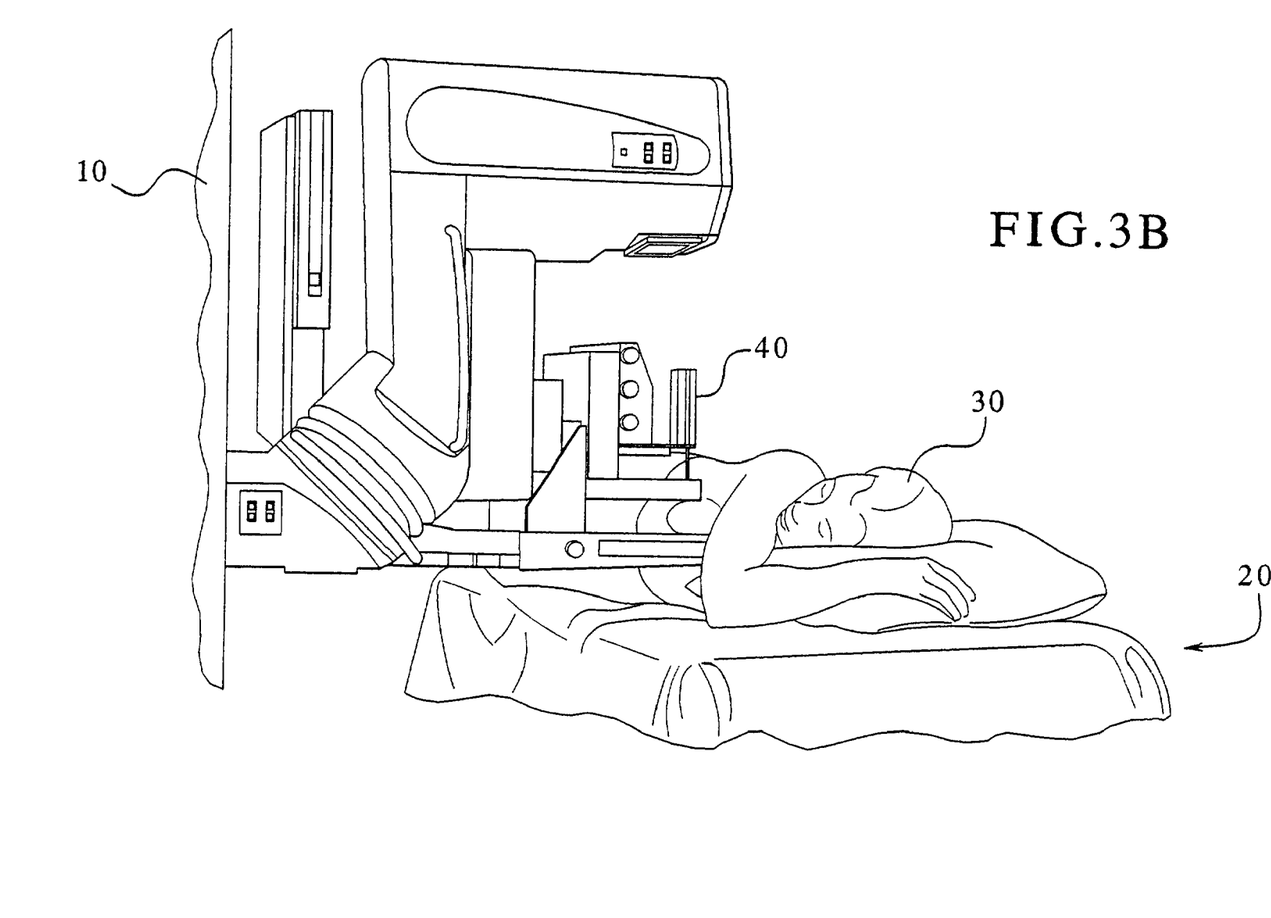
FIG. 3B is a schematic representation of a frontal view of a patient on the treatment platform in a patient lying or bed position relative to a cut away view of the rotatable/positionable digital mammography unit with a biopsy device.
Figure 3C:
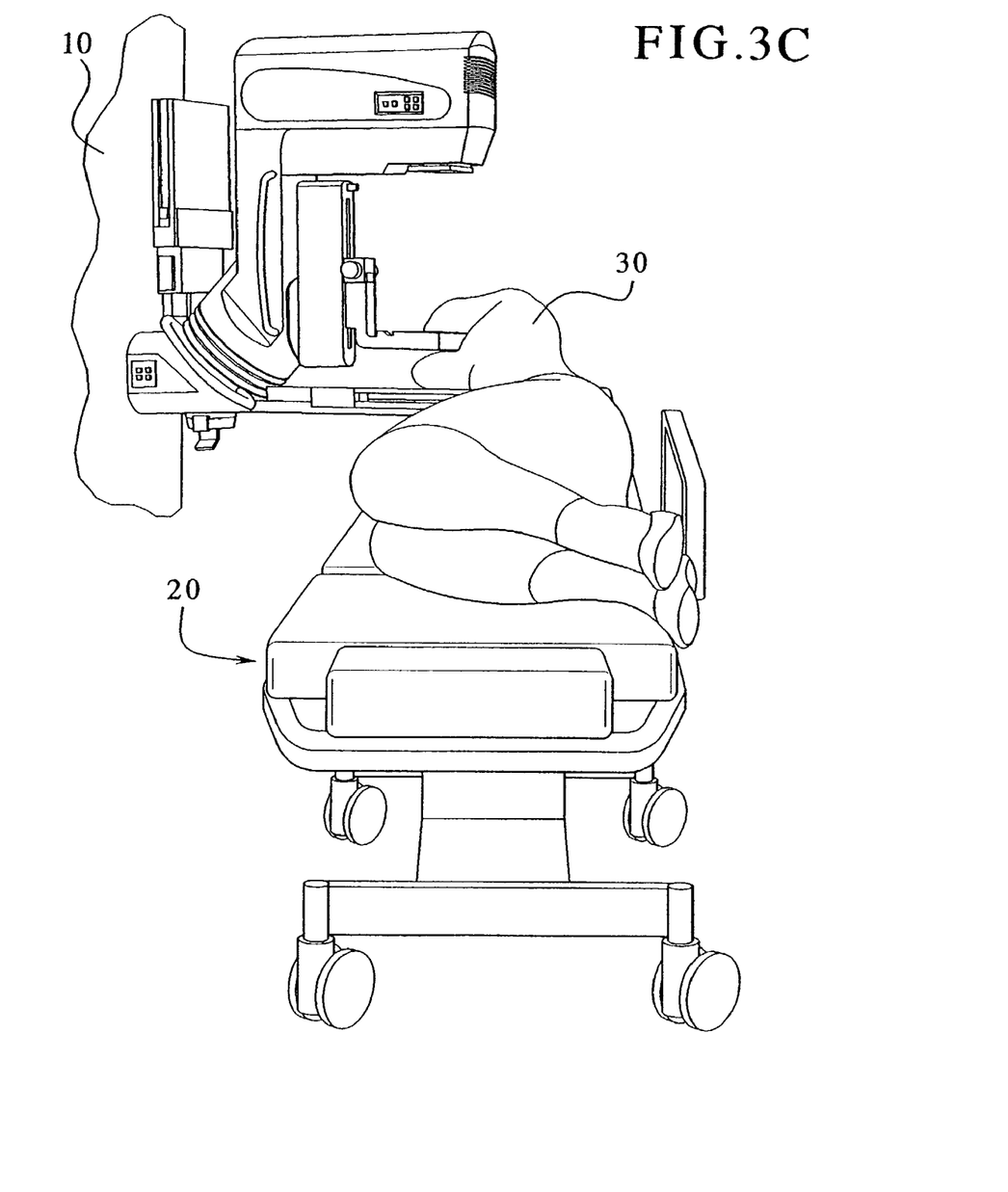
FIG. 3C is a schematic representation of a rear view of a patient on the treatment platform in a patient lying or bed position relative to a cut away view of the rotatable/positionable digital mammography unit.

FIG. 3B is a schematic representation of a frontal view of a patient 30 on a treatment platform 20 in a patient lying or bed position relative to a cut away view of the rotatable/positionable digital mammography unit 10 with an attached biopsy device 40. FIG. 3C is a schematic representation of a rear view of a patient 30 on a treatment platform 20 in a patient lying or bed position relative to a cut away view of the rotatable/positionable digital mammography unit 10.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A method for performing interstitial laser therapy and adjunctive therapy on a patient, comprising the steps of:
   a) placing the patient on an apparatus comprising:
      1) a mammography unit;
      2) an interstitial laser treatment device adjacently attached to the mammography unit in a single treatment unit,
         wherein the interstitial laser treatment device comprises a laser probe; and
      3) a treatment platform positioned relative to the mammography unit to enable the interstitial laser therapy to be performed,
      wherein the apparatus is located in a single treatment room,
      wherein the treatment platform comprises a first platform surface, and
      wherein adjunctive therapy may be performed in the treatment room without transferring the patient to a second platform surface;
   b) performing a mammographic examination on the patient;
   c) analyzing results from the mammographic examination; and
   d) performing interstitial laser therapy alone or interstitial laser therapy with adjunctive therapy on the patient, wherein the single treatment unit is capable of performing the mammographic examination and interstitial laser therapy in sequence.

2. The method of claim 1, wherein the mammography unit is a rotatable/positionable digital mammography unit.

3. The method of claim 1, wherein the interstitial laser treatment device further comprises a temperature probe.

4. The method of claim 1, wherein the treatment platform has at least two positions including a patient lying position and an inverted head position.

5. The method of claim 1, wherein the treatment platform has at least three positions including a patient sitting position, a patient lying position and an inverted head position.

6. The method of claim 1, wherein the treatment platform is supported on wheels.

7. The method of claim 6, wherein the wheels comprise a stationary mechanism.

8. The method of claim 7, wherein the stationary mechanism is selected from the group consisting of a locking, mechanism, a positioning mechanism and combinations thereof.

9. The method of claim 1, wherein the adjunctive therapy comprises axillary node dissection or sentinel node biopsy.

10. The method of claim 1, wherein the mammography unit is a rotatable/positionable digital mammography unit;
   wherein the interstitial laser treatment device further comprises a temperature probe;
   wherein the treatment platform has at least three positions including a patient sitting position, a patient lying position and an inverted head position; and
   wherein the adjunctive therapy comprises axillary node dissection or sentinel node biopsy.

11. An apparatus for performing interstitial laser therapy and adjunctive therapy on a patient, comprising:
   a) a mammography unit;
   b) an interstitial laser treatment device adjacently attached to the mammography unit in a single treatment unit, wherein the single treatment unit is capable of performing a mammographic examination and interstitial laser therapy in sequence,
   wherein the interstitial laser treatment device comprises a laser probe; and
   c) a treatment platform positioned relative to the mammography unit to enable the interstitial laser therapy to be performed,
   wherein the apparatus is located in a single treatment room,
   wherein the treatment platform comprises a first platform surface, and
   wherein adjunctive therapy may be performed in the treatment room without transferring the patient to a second platform surface.

12. The apparatus of claim 11, wherein the mammography unit is a rotatable/positionable digital mammography unit.

13. The apparatus of claim 11, wherein the interstitial laser treatment device further comprises a temperature probe.

14. The apparatus of claim 11, wherein the treatment platform has at least two positions including a patient lying position and an inverted head position.

15. The apparatus of claim 11, wherein the treatment platform has at least three positions including a patient sitting position, a patient lying position and an inverted head position.

16. The apparatus of claim 11, wherein the treatment platform is supported on wheels.

17. The apparatus of claim 16, wherein the wheels comprise a stationary mechanism.

18. The apparatus of claim 17, wherein the stationary mechanism is selected from the group consisting of a locking mechanism, a positioning mechanism and combinations thereof.

19. The apparatus of claim 11, wherein the adjunctive therapy comprises axillary node dissection or sentinel node biopsy.

20. The apparatus of claim 11, wherein the mammography unit is a rotatable/positionable digital mammography unit;
   wherein the interstitial laser treatment device further comprises a temperature probe;
   wherein the treatment platform has at least three positions including a patient sitting position, a patient lying position and an inverted head position; and
   wherein the adjunctive therapy comprises axillary node dissection or sentinel node biopsy.

* * * * *